(12) United States Patent  
Plateroti

(10) Patent No.: US 7,914,550 B2
(45) Date of Patent: Mar. 29, 2011

(54) METHOD OF TREATMENT WITH THE COMBINATION OF A GEM OR A CRYSTAL REMOVABLY ATTACHED WITH A MECHANICAL COUPLING DEVICE TO AN ACUPUNCTURE NEEDLE OR TO A VIBRATORY DEVICE FOR ACUPRESSURE TREATMENT

(76) Inventor: Aracely P. Plateroti, Atascadero, CA (US)

( * ) Notice: Subject to any disclaimer, the term of this patent is extended or adjusted under 35 U.S.C. 154(b) by 730 days.

(21) Appl. No.: 11/972,850

(22) Filed: Jan. 11, 2008

(65) Prior Publication Data

US 2009/0024160 A1    Jan. 22, 2009

Related U.S. Application Data

(62) Division of application No. 10/631,433, filed on Jul. 31, 2003, now Pat. No. 7,344,552.

(51) Int. Cl.
*A61B 17/00* (2006.01)
(52) U.S. Cl. ...................................................... 606/204
(58) Field of Classification Search ................. 606/191, 606/202, 203, 204, 204.15, 204.45, 204.55; 601/17–19, 134, 154; 215/382
See application file for complete search history.

(56) References Cited

U.S. PATENT DOCUMENTS

| 4,262,672 A | 4/1981 | Kief |
| 4,319,574 A | 3/1982 | Sun |
| 4,479,495 A | 10/1984 | Isaacson |
| 5,138,172 A | 8/1992 | Kropp |
| 5,520,617 A | 6/1996 | Wei |
| 5,904,700 A | 5/1999 | Guo |
| 6,022,368 A | 2/2000 | Gavronsky |
| 6,074,410 A | 6/2000 | Kim |
| 6,132,452 A | 10/2000 | Pinter |
| 6,203,562 B1 | 3/2001 | Ohkubo |
| 2003/0010744 A1* | 1/2003 | Ma et al. ................... 215/382 |
| 2005/0043753 A1* | 2/2005 | Rabiner et al. ............. 606/204 |

OTHER PUBLICATIONS

"Love Is in the Earth-A Kaleidoscope of Crystals Update" by Melody, published by Earth-Love Publishing House (1995) pp. Title, ISBN, 69-76.

"The Book of Crystal Healing" by Liz Simpson, Sterling Publishing Co, Inc. (1997) pp. Title, ISBN, 11-14 and 68-69.

* cited by examiner

*Primary Examiner* — Kevin T Truong

(74) *Attorney, Agent, or Firm* — Gramham S. Jones, II

(57) ABSTRACT

A mechanical coupling device is provided for temporarily interconnecting a gem or a crystal to be used for acupressure treatment to a vibration generating device. Alternatively a mechanical coupling device is provided for temporarily interconnecting the handle of an acupuncture needle to a gem or a crystal. The mechanical coupling device can be a helical or spiral, metal wire, a cylindrical linkage, a conical linkage or a clamp connecting the acutreatment device to the other element. The method employed is to apply the acutreatment devices to acupoints of a patient with the above devices including the combination of a gem or a crystal interconnected to an acupuncture needle or a vibration generating device interconnected to an acupressure gem or crystal.

21 Claims, 6 Drawing Sheets

METHOD OF TREATMENT WITH THE COMBINATION OF A GEM OR A CRYSTAL REMOVABLY ATTACHED WITH A MECHANICAL COUPLING DEVICE TO AN ACUPUNCTURE NEEDLE OR TO A VIBRATORY DEVICE FOR ACUPRESSURE TREATMENT

This application is a division of Ser. No. 10/631,433 filed 31 Jul. 2003 now U.S. Pat. No. 7,344,552.

BACKGROUND OF THE INVENTION

1. Field of the Invention

This invention relates to acupuncture and acupressure and more particularly to improvements in methods and apparatus for performing acupuncture and acupressure.

2. Description of Related Art

Acupuncture

The treatment of physiological disorders by means of acupuncture is well known. Acupuncture is the method of inserting needles into the skin at exact, spatially defined points known as acupoints in order to treat or avert specific disorders of the human body. An acupuncture needle (acu-needle) used in clinical acupuncture practice, which is usually composed of a metal such as silver, may be composed of other metals such as gold, platinum, copper or stainless steel. In ancient practice of the art of acupuncture needles were made of bone and other materials. The head or handle of the acu-needle can be formed of finely woven thread silver over the external surface of the shaft. A skilled practitioner is generally required to administer acupuncture treatment.

Acupressure Contrasted with Acupuncture

An alternative to acupuncture is acupressure, the application of external pressure to the surfaces of the body of a human being or an animal at the traditional acupuncture points. Acupressure has been employed in lieu of acupuncture where it is not possible or acceptable to employ acupuncture.

U.S. Pat. No. 6,022,368 of Gavronsky et al entitled "Acupuncture method and device states that the "classical Chinese explanation is that channels of energy run in regular patterns through the body and over its surface. These channels, called meridians, are like rivers flowing through the body to irrigate and nourish the tissues. Blood flow and nervous pulses also follow meridians to run through the body to various parts, structures and organs. An obstruction in the movement of these energy rivers is like a dam that backs up the flow in one part of the body and restricts it in others. Any obstruction and blockages or deficiencies of energy, blood and nervous pulses would eventually lead to disease."

"The meridians can be influenced by needling the acupuncture points: the acupuncture needles unlock the obstruction at the dams, and reestablish the regular flow through the meridians. Acupuncture treatment can, therefore, help the body's internal organs to correct imbalances in their digestion, absorption, and energy production activities, and in circulation of their energy through the meridians."

"Modern science explains the functions of acupuncture in two major ways:

"1. Needling the acupuncture points stimulates the nervous system to release chemicals in the muscles, spinal cord, and brain. These chemicals will either change the sensation of pain, or they will trigger the release of other chemicals and hormones which influence the body's own internal regulating system."

"2. Modern science reveals that the very basic unit of the body is [the] cell. Cells' movement follow the movement of electrons. The electrons inside the cell act according to their own regular patterns. We call all these electrons in a living body, bioelectrons."

"Energy flow in the meridians is the direct or indirect transportation of Bioelectrons.' Meridians are the pathways where bioelectrons move more frequently than in other parts of the body. When positive and negative charges in the bioelectronic movements are not balanced, the cells would act abnormally."

"All the external factors, such as mechanical, physical, chemical, biological and internal factors such as mental, hereditary, constitutional can cause and force the body's bioelectrical movement turn to imbalance and would lead to a disease."

Pointing out the acceptance of acupuncture therapy in the United State, U.S. Pat. No. 6,022,368 of Gavronsky et al states "Acupuncture or needle therapy for treating various ailments have been known for at least four thousand years. Different materials, including stone, wood and, in recent years, metal were used for manufacturing acupuncture needles. Twentieth century discoveries in biomedicine gave better understanding about transmission of the infectious diseases. Based on this knowledge, new much stricter requirements for safety and sterility during acupuncture procedure were imposed. Modern day acupuncturists in the USA and other developed countries use sterile, disposable needles made of stainless steel or, sometimes, other metals. In 1996, FDA has approved acupuncture needles as medical equipment, acknowledging safety and effectiveness of the procedure. Many hospitals have started incorporating acupuncture as part of their services over last years."

In addition, U.S. Pat. No. 6,022,368 of Gavronsky et al states "For the acupuncture prospective, various types of temperature modifying tools have been used in acupuncture for centuries. They were used to enhance the therapeutic effect of the acupuncture treatment. External application of heat and heat generating herbs were utilized to produce a physiological response to that obtained during treatment with warm water. A special herb, Artemisia Vulgaris, which is burnt on or over the skin, infrared heaters, herbal compresses with warming properties are among popular acupuncturist tools for altering temperature. At the same time, if a patient is placed in a tub in which temperature can be controlled, a guaranteed systemic response in the patient is assured, and the bodily processes can be shifted in a desired direction. A good example from the clinical practice is the acupuncture treatment of the muscular and skeletal problems. The muscular and skeletal conditions, with damage limited primarily to soft tissues, respond extremely well to a combination of acupuncture with heat. Both methods enhance the blood circulation, relax muscles and tendons, increase the metabolic rate, and promote healing. Low back pains, sprains, strains, repetitive motion disorders, and many others fall into this category."

U.S. Pat. No. 4,262,672 of Kief entitled "Acupuncture Instrument" describes an acupuncture instrument comprising a needle having a head and an electrical connection for applying a transformer arrangement including an electric coil constituting a secondary winding of the transformer arrangement and having two poles, one of the poles being insulated therefrom, the electric coil being arranged on the needle head and being capable of being surrounded by another coil constituting a primary winding of the transformer arrangement, and an annular electrode electrically connected to the other pole of the secondary winding and insulated therefrom, and vertically movably arranged on the secondary winding.

Acupuncture, Acupressure and Acupoints

U.S. Pat. No. 4,479,495 of Isaacson October entitled "Acupressure Point Stimulator Device" states that "the traditional theory of acupuncture and its delineation of point locations are identical in acupressure, the only difference being that in acupressure, only pressure is applied to the selected points. While this pressure is not sufficient to puncture the skin, it still is an effective treatment for certain disorders. For this reason, the terms 'acupuncture point, and 'acupressure point' are used interchangeably to denote an identical and specific body point. The term 'acupoint' also may be used to denote these body points. Since the vast majority of the traditional literature on the subject of acupoints relates to the practice of acupuncture, most acupressure theory is simply transposed or extrapolated from this greater and older school of knowledge. One notable difference between acupuncture and acupressure is that acupressure, by virtue of its lack of puncturing the skin, relieves muscular tension while also contacting the traditional energy pathways of acupuncture. For example, one acupressure device, shown in U.S. Pat. No. 4,319,574 to Sun is arranged to apply pressure to points on the external ear, thereby employing an acupuncture specialty known as auricular therapy. However, the disadvantage of this device is that it is mainly useable on the ear only, and not at most other acupoints on the body. Particularly, it is not applicable to the most effective acupoints, which are located on the limbs, specifically the areas between the knees and toes and the areas between the elbows and fingertips. Also, the traditional literature of acupuncture often specifies various angles of insertion of needles to effectively stimulate a given acupoint for respective therapeutic results. Likewise, in acupressure, pressure is applied at various angles at a given acupoint for differing therapeutic considerations."

Application Laser Energy to Acupoints

U.S. Pat. No. 5,138,172 of Kropp entitled "Apparatus and Method for Applying Information Energy to a Substrate" describes application of laser energy to acupuncture points by "modulating a 632.8 nm laser beam by already energized substrates in the cuvettes . . . whereby the modulated laser beam is directed along the axis Lx on specific accupuncture [sic] or diacra points of a human body absorbing the energized frequency combination transferred from the substrate."

Contacting Acupoints on Body with Crystals without Acupuncture

US. Pat. No. 6,203,562 of Ohkubo entitled "Appliance for Medical Treatment" describes a medical treatment appliance for performing therapeutic treatment by slightly pushing the appliance onto the skin of a patient. Ohkubo states that "In conventional finger pressure therapy, a nerve is stimulated and a blood flow is accelerated by massaging an affected parts of a human body and an effective spot with human hand or fingers to mitigate the pain. The acupuncture therapy applies needle or moxa heating to an affected portion or an effective spot to perform treatment using heating power." Ohkubo states further that the "conventional finger pressure therapy is effective in mitigating a stiff-shoulder pain, a muscular pain, etc., but it takes a long time . . . " Then Ohkubo states "The ailment can be cured without causing pain of human body, just by applying medical treatment appliance in contact with the affected portions and pushing slightly to a skin of a patient to enhance a natural healing power of human body and to relieve pains . . . unlike electric medical instrument, it also does not use any external electricity. It is intended to introduce a medical treatment appliance that can give epoch-making treatment results. The appliance includes a grip portion, a conductor portion consisting essentially of electrically conductive metal(s), a 'different metal' portion having an ionization tendency different from the electrically conductive metal (s), and optionally a crystal portion consisting essentially of a mineral, wherein the 'different metal' portion, and optionally the crystal portion is (are) attached to the conductor portion. The crystal portion has been pressure-attached to the grip portion by a burning method and fixed, and thereby, the crystal portion is compressed, and as a result, the crystal surface is electrified due to a piezo-electric effect. When the conductor portion and/or the 'different metal' portion is(are) slightly pushed to the affected portion, a tip of the crystal portion also simultaneously contacts a skin of a patient, and the electricity generated in the crystal portion is discharged into the body of the patient, and thus a weak electric current flows, which enhances said therapeutic effect."

U.S. Pat. No. 6,132,452 Pinter "Method and Device for Promoting Energy Flow in an Organism" states that "The foundations of bioelectric therapy, electromagnetic therapy, electrocrystal therapy and color/light therapy are posited upon all living organisms being formed from atoms or particles, each of which carries energy, and which together form substances through association with one another by the action of an electrical force thereon . . . modern physics has provided insight into the inherent vibration of the living building blocks of nature—the oscillating or vibrating nature of nuclei, atoms and cells. These building blocks as well as the large structures of which they are parts have a natural resonance—an easy and natural way of being. On the other hand, all structures, in addition to having a harmonious natural resonant frequency, can vibrate at dissonant frequencies. It is this nature of movement of energy which gives rise to harmonious or disharmonious, to the positive and negative aspects of health and environment. With respect to electrocrystal therapy, a crystal is a form of solid matter in which virtually all the atoms and molecules are ordered and structured—a naturally harmonious form. Such crystals can act as crystal frequency generators when an electric potential is applied to them. Thus, when a crystal is placed adjacent to other forms of matter, particularly living matter, and an electric potential is applied to it, the crystal can create harmonious resonance in sub-atomic vibration of neighboring living matter."

Application of Magnetic Fields to Acupoints

U.S. Pat. No. 5,904,700 of Guo entitled "Magnetic Acupuncture Pointer" describes a magnetic pointer apparatus of traditional Chinese medicine for health care, and in particular, relates to a magnetic medicine instrument of acupuncture. The pointer apparatus includes an air bag, and a permanent magnetic head provided within the hollow case. To operate the pointer, while the hollow case is attached close to the acupuncture point of human body, the air bag is pressed at the same time. When the pressure is released, the air bag restores to the original shape and the air within the hollow case is sucked into said bag, causing the magnet head to be closely attached to the acupuncture point of human body. The pointers with N pole and S pole may be positioned on both sides of human body making vertical cutting lines of magnetic force acting upon the human body."

Healing with Crystals

"Love Is in the Earth-A Kaleidoscope of Crystals Update" by Melody, published by Earth-Love Publishing House (1995) pp. 69-76 describes chakras which are "intersections of vital energy flows present in the ethereal body and in related locations in the physical body." At page 74, it states "'Laying-on of Stones' . . . involves placing members of the mineral kingdom upon the body of another. Those from ancient civilizations have used this art to facilitate healing of another on all levels . . . promoting the energy transfer from the minerals to the physical form." At page 76, it is stated "Silver, gold, copper, or platinum used on a crystalline form or as a wand [with a natural crystal, faceted gem, or polished mineral located at one or both ends] facilitates amplification of the energies of the crystalline form, promoting maximum utilization of the potential energy. The energies associated with the miner comprising the wand also supplement those of the contained minerals . . . . The 'whirling wand', . . . produces an amplification and directed-ness of the mineralogical components. The structure provides the energy of a "spiral", bringing synthesis to the energies of the physical plane and the spiritual worlds. The energies of the attached minerals are enhanced by this design, allowing for intensification and sensitivity with respect to the direction of energy transmission." The concept of a "spiral" as employed elsewhere in the volume clearly pertains to a non-physical meaning, i.e. spirituality, as contrasted with a physical spiral.

"The Book of Crystal Healing" by Liz Simpson, Sterling Publishing Co, Inc. (1997) pages 11-14 and 68-69 describes use of crystals for crystal healing in connection with the life force of "'chi', pure Consciousness, prana, the Universal Field . . . this universal source of life courses through all things and in dosing so produces an outer energy field referred to as 'aura'. This is often depicted as halos surrounding the bodies of holy people . . . you also have an aura. And it is this which allows you to interact on a non-physical level with all things . . . that everything in the universe vibrates, albeit at different frequencies." At pages 68-69, seven major chakras of the body and crystals which are appropriate for use therewith are described.

FIG. 1A shows a first prior art acupuncture needle 10 comprising an acupuncture wire 11, a handle 12 thereabove and a tail 12T at the top end of the handle 12.

The acupuncture wire 11 of the needle 10 is preferably straight and is preferably composed of extremely fine stainless steel, having a very thin diameter. Acupuncture wire 11 is composed of a needle body 11B, a tip 11T at the bottom of the needle body 11B and a root 11R at the top of the needle body 11B. The needle body 11B has a sharp point at the distal portion thereof traditionally referred to as the needle tip 11T, which should be as sharp as a pine needle. The root 11R is the demarcation line between the needle body 11B and the handle 12.

The handle 12, which is webbed with filigree of either copper or stainless steel, has a larger diameter suitable for manipulation. A cap 12C is formed at the top of the tail 12T. The needle 10, which is sterile, is packaged in a sterile envelope (not shown).

FIG. 1B shows a second prior art acupuncture needle 20 comprising an acupuncture wire 21, with a handle 22 thereabove and with a tail 22T at the top end of the handle 22.

The acupuncture wire 21 of the needle 20 is preferably straight and is preferably composed of extremely fine stainless steel, having a very thin diameter. Acupuncture wire 21 is composed of a needle body 21B, a tip 21T at the bottom of the needle body 21B and a root 21R at the top of the needle body 21B. The needle body 21B has a sharp point at the distal portion thereof traditionally referred to as the needle tip 21T, which should be as sharp as a pine needle. The root 21R is the demarcation line between the needle body 21B and the handle 22.

The handle 22, which is composed of metal has a larger diameter suitable for manipulation. No cap is formed at the top of the tail 22T. The needle 20, which is sterile, is packaged in a sterile envelope (not shown).

SUMMARY OF THE INVENTION

Glossary

Acupoint specific area on the body

Acupressure massage with fingers (as in Shiatsu) or a device at specific areas of the body as done with acupuncture Acupuncture puncturing the body with needles at specific points known as acupoints to cure disease or to relieve pain Acutreatment treatment at acupoints by acupressure and/or acupuncture Chakra any of several points of physical or spiritual energy in the human body according to yoga philosophy Gem a precious or semiprecious stone or crystal of the kind employed in acutreatment and/or laying-on-of stones as described in "Love Is in the Earth-A Kaleidoscope of Crystals Update", supra and "The Book of Crystal Healing", supra Shiatsu massage with the fingers applied to those areas of the body used in acupuncture In the past while laying on of gems or stones and use of acupuncture and acupressure have been employed, the ability to provide a structure combining laying on of gems or stones with acupuncture or acupressure has not be contemplated over the centuries of performing these arts of physical therapy.

It is an object of this invention to provide a method and a means for applying energy from gems and stones to acupuncture needles and acupressure devices.

In accordance with this invention, a linkage for interconnecting an acutreatment device selected from the group consisting of an acupressure and acupuncture device is provided comprising a mechanical coupling device bonded to a first element. The mechanical coupling device is adapted for being temporarily joined to a second element where one of the first element and the second element is an acutreatment device.

In one preferred embodiment, the second element is an acupuncture device and the first element is an element selected from the group consisting of gems and crystals and preferably the mechanical coupling device comprises a metal structure bonded to the second element and preferably the linkage comprises a spiral, metal wire bonded to the second element which is preferably a helical or spiral metal wire connected to the first element.

In another preferred embodiment the second element is an acupressure element selected from the group consisting of gems and crystals, and the mechanical coupling device comprises a metal structure bonded to the second element.

Preferably, the first element is a vibration generating device, and the second element is an acupressure element selected from the group consisting of gems and crystals, and the mechanical coupling device comprises a spiral, metal wire bonded to the second element.

Preferably, the mechanical coupling device comprises a metallic cylinder or cone connected to said first element; a metallic clamp connected to said first element, and a slidable and/or readily releasable connection to a second element where one of the first element and the second element is an acutreatment device.

Another aspect of this invention is a method of acutreatment selected from the group consisting of an acupressure and acupuncture device comprising providing a first element and the second element where one thereof is an acutreatment device, temporarily joining a mechanical coupling device bonded to said first element with said mechanical coupling device being adapted for being joined to the second element where one of the first element and the second element is an acutreatment device, and then applying the acutreatment device to an acupoint on a patient.

Preferably, the second element is an acupuncture device and the first element is an element selected from the group consisting of gems and crystals. It is preferred that the mechanical coupling device comprises a metal structure bonded to the second element such as a helical or spiral metal wire bonded to the second element.

An alternative to the method is to employ an acupressure element as the second element is selected from the group consisting of gems and crystals, and the mechanical coupling device comprises a metal structure bonded to the second element.

BRIEF DESCRIPTION OF THE DRAWINGS

The foregoing and other aspects and advantages of this invention are explained and described below with reference to the accompanying drawings, in which.

DESCRIPTION OF THE PREFERRED EMBODIMENT

I have discovered that the combination of an acupuncture needle with a gem installed thereon by a mechanical coupling device of the kinds shown in FIGS. 2A and 2B, and FIGS. 3-9 has greatly enhanced the therapeutic benefit of acupuncture. The method of acupuncture in this case is to perform a temporary installation, i.e. assembly, of the mechanical coupling device of FIGS. 2A, 2B and 3-9 carrying a gem on an acupuncture needle and then to insert the acupuncture needle into the acupoint of the patient with the energy from the gem enhancing the acupuncture treatment.

Figures 1A, 1B, 2A, 2B:
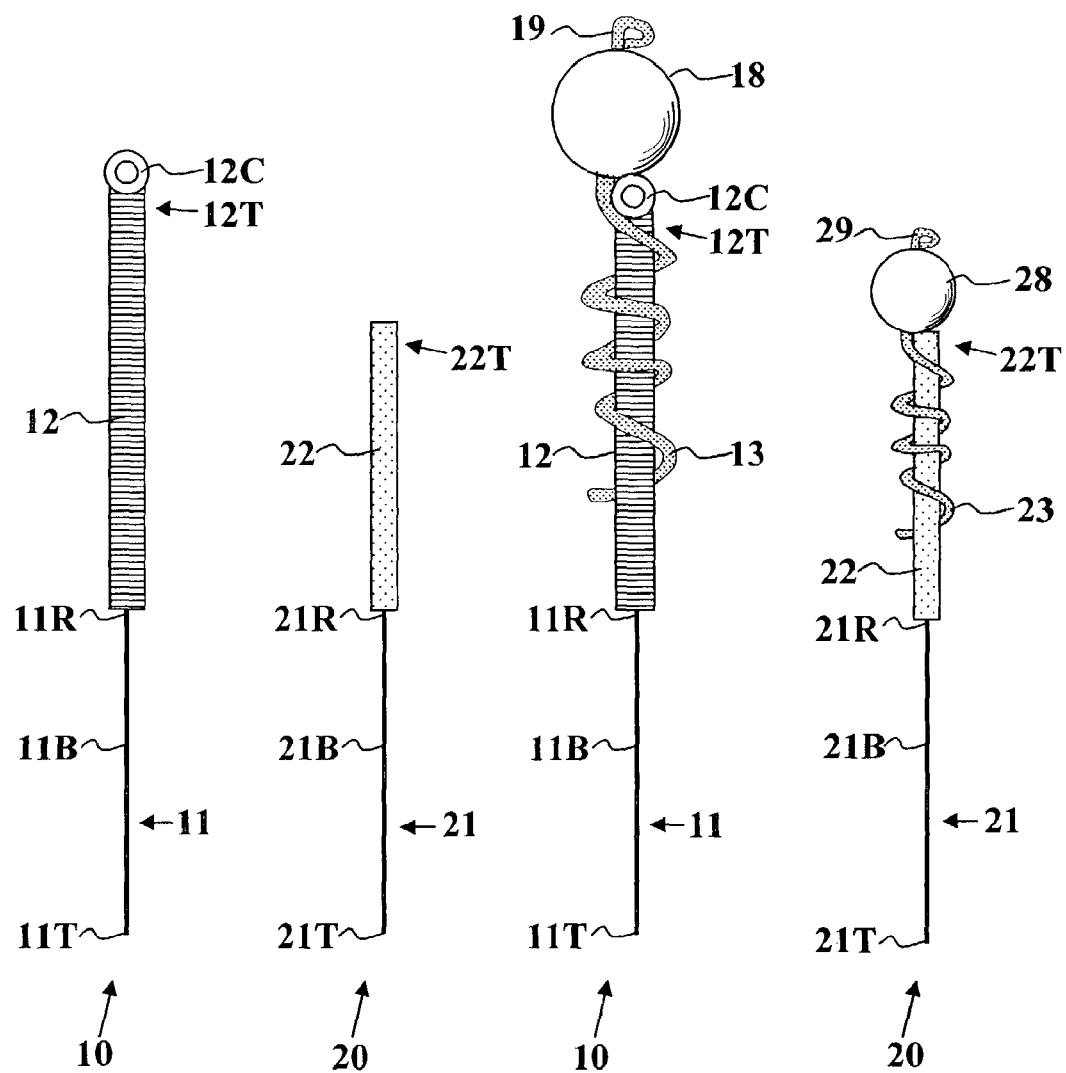
FIG. 1A shows a first prior art acupuncture needle having a needle body at the bottom with a very thin diameter, a handle with a larger diameter suitable for manipulation and a cap formed on the top of the handle.
FIG. 1B shows a second prior art acupuncture needle having a needle body at the bottom with a very thin diameter, and a smaller handle with a larger diameter suitable for manipulation, but without a cap.
FIG. 2A shows the acupuncture needle of FIG. 1A, which has been modified by the temporary assembly over the tail and the handle of the needle of a readily removable helical or spiral wire that carries a gem on top thereof.
FIG. 2B shows the acupuncture needle of FIG. 1B which has been modified by the temporary assembly over the tail and the handle of the needle of a readily removable helical or spiral wire which carries a gem on top thereof.

FIG. 2A shows the acupuncture needle 10 of FIG. 1A, which has been modified by the temporary installation, i.e. assembly, therewith over the tail 12T and the handle 12 of the needle 10 of a, metallic, helical or spiral wire 13, which carries a gem 18, which is preferably crystalline, i.e. a crystal, on top thereof.

The gem 18 is defined herein to includes crystals, gems and stones as those employed in "laying-on-of-stones". In that connection the description of stones and crystals in "Love Is in the Earth-A Kaleidoscope of Crystals Update", supra and "The Book of Crystal Healing", supra is incorporated herein by reference.

As in FIG. 1A, the acupuncture needle 10, which is sterile, has a very thin diameter body 11B at the bottom of the handle 12. The handle 12 has a larger diameter than the wire 11 of the body 11B suitable for manipulation of the needle 10. A cap 12C is formed on the top of the handle 12 above the tail 12T. The needle 10 is packaged in a sterile envelope. The body 11B has a very thin diameter and is preferably composed of extremely fine stainless steel.

In FIG. 2A, in accordance with this invention, a helical or spiral wire 13 passes through a hole through the gem 18, which ends at the twisted top 19 of the wire 13 thereby securely attaching the gem 18 to the wire 13. The helical or spiral wire 13 is shown supporting the gem 18 in the temporary installed position, with the wire 13 wrapped about the handle 12, the tail 12T and the cap 12C of the acupuncture needle 10. According to one aspect of the method of this invention, the helical or spiral wire 13 has been temporarily installed over the handle 12 holding the gem 18 in contact with the cap 12C of the acupuncture needle 10. The helical or spiral wire 13 has an inner diameter adapted for being temporarily assembled with the acupuncture needle by sliding the helical or spiral wire 13 over the cap 12C, so that it fits securely around the handle 12 of the acupuncture needle 10 during treatment of a patient, but the helical or spiral wire can be removed immediately for use with another acupuncture needle 10 by sliding thereof up off the handle 12, the tail 12T and the cap 12C. In other words, the helical or spiral wire 13 and the gem 18 are removably mounted in intimate contact with the handle 12 permitting energy from the gem 18 to be transmitted therefrom through the helical or spiral metal wire 13, the metallic handle 12 to the metallic body 11 of the acupuncture needle 10. The helical or spiral wire 13 is preferably composed of a metal such as stainless steel, gold filled (i.e. a layer of a gold alloy joined to a base metal alloy, where the base metal is selected from the group consisting of copper, zinc and brass) or sterling silver.

FIG. 2B shows the acupuncture needle 20 of FIG. 1B, which has been modified by the assembly therewith over the handle 22 of the needle 20 of a helical or spiral wire 23 which carries a gem 28 on top thereof. The helical or spiral wire 23 passes through a vertical hole through the gem 28 that ends at the twisted top 29 of the wire 23 thereby attaching the gem 28 to the spiral wire 23 and the helical or spiral wire 23 is shown wrapped about the handle 22 of acupuncture needle 20. The helical or spiral wire 23 has been temporarily installed over the handle 22 holding the gem 28 in close proximity with the tail 22T at the top end of the handle 22 and preferably in contact with the tail 22T at top of the acupuncture needle 10. The helical or spiral wire 23 has an inner diameter adapted for being assembled with the acupuncture needle 20 by sliding the helical or spiral wire 23 over the top of handle 22 for temporarily fitting securely around the handle 22 of the acupuncture needle 20, but immediately removable by sliding thereof up off the handle 22, as in the case of the embodiment of FIG. 2A.

Figures 3, 4, 5, 6:
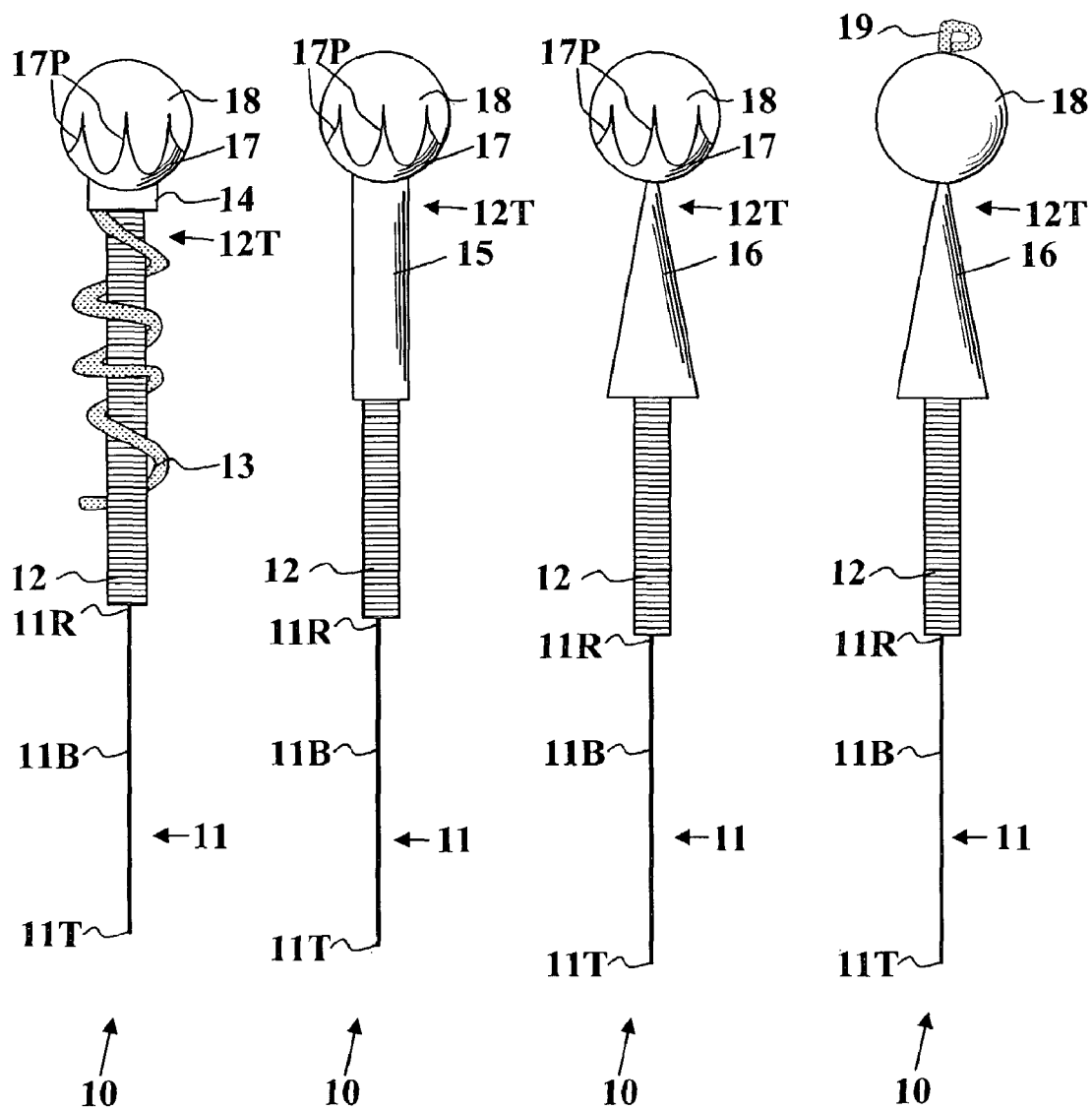
FIG. 3 shows the acupuncture needle of FIG. 1A, which has been modified, in accordance with this invention, by the assembly therewith over the handle of the needle of another helical or spiral-wire, which carries the gem on top thereof, but which in this case is the wire is bonded to a mounting base covering the cap formed on top of the handle.
FIG. 4 is a modification of FIG. 3 where a cylinder which replaces the helical or spiral wire comprises an extension of the cylindrical mounting base in FIG. 3.
FIG. 5 is a modification of FIG. 3, wherein a conical element replaces the helical or spiral wire, with the conical element comprising an extension of the cylindrical mounting base in FIG. 3.
FIG. 6 is a modification of FIG. 5 where the conical element is secured to the gem by means of a wire bonded thereto, which passes through a hole drilled through the gem and as in the case of FIG. 5, the conical element and the gem are removably mounted, but are in intimate contact with the handle of the needle to facilitate transmission of energy from the gem to the body and the tip of the acupuncture needle.

FIG. 3 shows the acupuncture needle 10 of FIG. 1A, which has been modified, in accordance with this invention, by the assembly therewith over the handle 12 of the needle 10 of another helical or spiral wire 13 which carries the gem 18 on top thereof, but which in this case the wire 13 is bonded to a cylindrical mounting base 14 which covers the cap 12C (not shown). That is to say that the helical or spiral wire 13 has been temporarily installed over the cap 12 at the top end of the handle 12. The gem 18 is securely attached to the mounting base 14 with conformal prongs 17 that hold onto the exterior surface of the gem 18. In other words, the prongs 17 attach the gem 18 to the mounting base 14. The gem 18 can be attached to the mounting base 14 by means which can include a pin inserted into the bottom of the gem 18. Alternatively, a bonding agent can be employed to fasten the gem 18 securely to the mounting base 14 and prongs 17. As in FIG. 2A, the acupuncture needle 10, which is sterile, has a very thin diameter body 11B, root 11R and needle tip 11T at the bottom. Formed above the body 11B is the handle 12 with a larger diameter suitable for manipulation. The needle 10 is packaged in a sterile, envelope. The body 11B has a very thin diameter and is preferably composed of extremely fine stainless steel.

In FIG. 3 unlike FIG. 2A, the helical or spiral wire 13 is bonded to the mounting base 14 by soldering or the like. As in FIG. 2A, the helical or spiral wire 13 is wrapped about the handle 12 and the cap 12C of the acupuncture needle 10. The helical or spiral wire 13 has an inner diameter adapted for being assembled with the acupuncture needle 10 by sliding the helical or spiral wire 13 over the cap 12C and to fit securely around the handle 12 of the acupuncture needle 10, but immediately removable by sliding thereof up off the handle 12. Energy from the gem is transmitted through the prongs 17 to the base 14 and helical or spiral wire 13 through the needle 11 to the body 11B and the tip 11T. As in the case of FIG. 2A, the helical or spiral wire 13 and the gem 18 are removably mounted, but are in intimate contact with the handle 12 to facilitate transmission of energy from the gem 18 to the body 11B and the tip 11T of acupuncture needle 10.

FIG. 4 is a modification of FIG. 3 wherein a cylinder 15 replaces the helical or spiral wire 13, with the cylinder 15 comprising an extension of the cylindrical mounting base 14 shown in FIG. 3. The prongs 17 provide secure attachment of the gem 18 to the cylinder 15. As in FIG. 3, energy from the gem 18 is transmitted through the prongs 17 to the cylinder 15 and from the cylinder 15 through the needle 11 to the body 11B and the tip 11T. As in the case of FIG. 3, the cylinder 15 and the gem 18 are removably mounted, but are in intimate contact with the handle 12 to facilitate transmission of energy from the gem 18 to the body 11B and the tip 11T of the acupuncture needle 10.

FIG. 5 is a modification of FIG. 3 wherein a conical element 16 replaces the helical or spiral wire 13, with the conical element 16 comprising an extension of the cylindrical mounting base 14 shown in FIG. 3 with the gem 18 securely attached to conical element 16. As in FIG. 3, energy from the gem 18 is transmitted through the prongs 17 to the conical element 16 and from the conical element 16 through the needle 11 to the body 11B and the tip 11T. As in the case of FIG. 3, the conical element 16 and the gem 18 are removably mounted, but are in intimate contact with the handle 12 to facilitate transmission of energy from the gem 18 to the body 11B and the tip 11T of acupuncture needle 10.

FIG. 6 is a modification of FIG. 5 where the conical element 16 is secured to the gem 18 by means of a wire 19 bonded thereto, which passes through a hole drilled through the gem 18 which securely attaches the gem 18 to the conical element 16. As in the case of FIG. 5, the conical element 16 and the gem 18 are removably mounted, but are in intimate contact with the handle 12 to facilitate transmission of energy from the gem 18 to the body 11B and the tip 11T of acupuncture needle 10.

Figure 7:
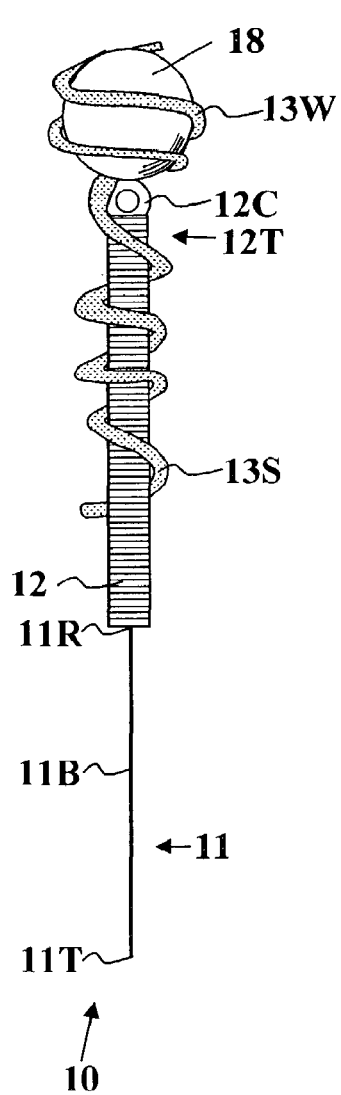
FIG. 7 shows a modification of FIG. 2A wherein the helical or spiral wire has been replaced by a helical or spiral wire which instead of passing through the gem, is wrapped about the gem, thereby clasping the gem firmly.

FIG. 7 shows a modification of FIG. 2A wherein the helical or spiral wire 13 is replaced by a helical or spiral wire 13S which instead of passing through the gem 18, is wrapped by winding section 13W about the gem 18, thereby clasping the gem 18 to secure it firmly.

Figure 8:
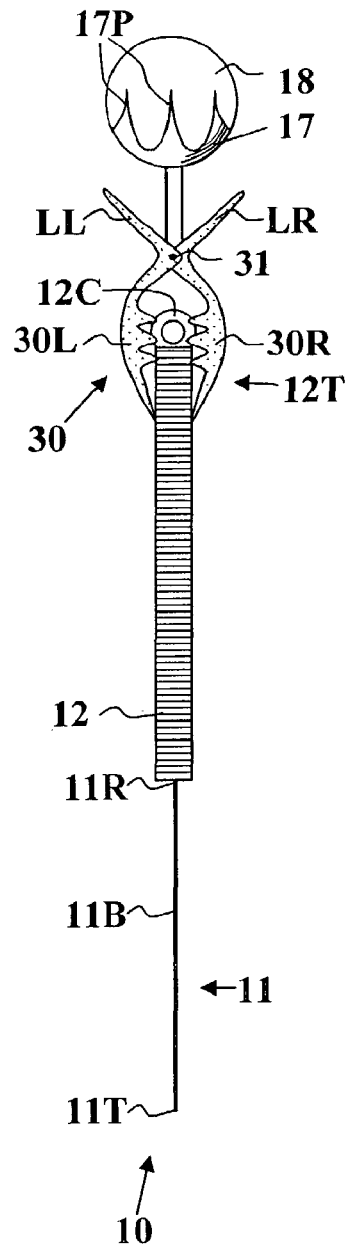
FIG. 8 shows a modification of FIG. 2A wherein the helical or spiral wire has been replaced by a spring biased clamp with a left arm and a right arm with a pivot pin therethrough above the cap of the needle.

FIG. 8 shows a modification of FIG. 2A wherein the helical or spiral wire 13 has been replaced by a spring biased clamp 30 with a left arm 30L, right arm 30R with a pivot pin 31 therethrough above the cap 12C of the needle 10. Arms 30L and 30R grasp the top of the needle 10, reaching down over the cap 12C of the needle 10. The left arm 30L includes a lever LL above the pin 31 and the right arm 30R includes a lever LR above the pin 31. By pressing the levers LL and LR of clamp 30, the spring-biased clamp can be lifted away from its grasp of the handle 12 of needle 10. The prongs 17 secure the gem 18 to the spring biased clamp.

Figure 9:
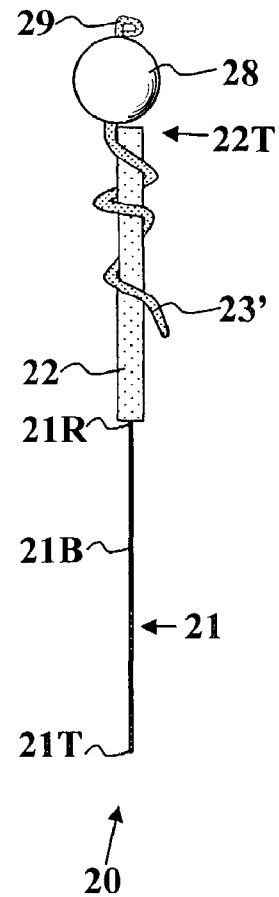
FIG. 9 shows a modification of FIG. 2B wherein the helical or spiral wire has only a few turns about the handle of the needle.

FIG. 9 shows a modification of FIG. 2B wherein the helical or spiral wire 23' secured to the gem 28 has only a few turns about the handle 22 of the needle 20. As in FIG. 1B the acupuncture needle 20 comprises an acupuncture wire 21 with a handle 22 with a tail 22T at the top end of the handle 22. Acupuncture wire 21 is composed of a needle body 21B, a tip 21T at the bottom of the needle body 21B and a root 21R at the top of the needle body 21B. The handle 22, which is composed of metal has a larger diameter suitable for manipulation. No cap is formed at the top of the tail 22T.

I have discovered that the combination of either of an acupuncture needle 10 (20) respectively with a gem 18 (28) installed thereon temporarily by a mechanical coupling device of the kinds shown in FIGS. 2A and 2B, and FIGS. 3-9 has greatly enhanced the therapeutic benefit of acupuncture by transmission to the needle 10 (20) of energy from the gem 18 (28), respectively. The method of acupuncture in this case is to install the mechanical coupling device 13, 14, 15, 16, 13W, 30 or 23' of FIGS. 2A, 2B and 3-9 (which is secured to a gem 18 (28)) on an acupuncture needle 10 (20) and then to insert the needle 10 (20) into the acupoint of the patient.

Figures 10A, 10B:
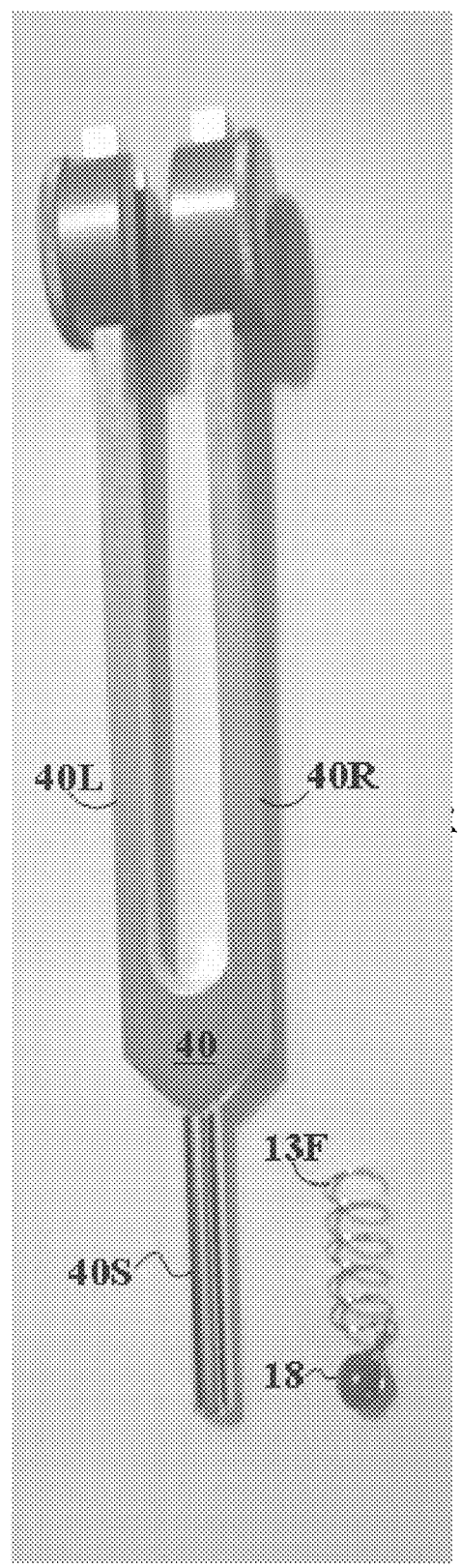
FIG. 10A shows a tuning fork for use with the acupressure device of FIG. 10B.
FIG. 10B is a photograph of an acupressure device comprising a helical or spiral metal coil and an acupressure gem connected as in FIG. 2A, that are adapted to be joined to the shaft of the tuning fork of FIG. 10A for use in acupressure treatment.

FIG. 10A shows a vibratory element comprising a tuning fork 40 for use with the acupressure appliance of FIG. 10B.

The fork 40, which includes a left prong 40L and a right prong 40R connected to a shaft 40S, is about six (6) inches long from top to bottom.

FIG. 10B is a photograph of an acupressure appliance comprising a helical or spiral coil 13F and an acupressure gem 18 securely connected as in FIG. 2A, which are adapted to be joined to the shaft 40S of the tuning fork 40 of FIG. 10A for use in acupressure treatment.

Figure 11:
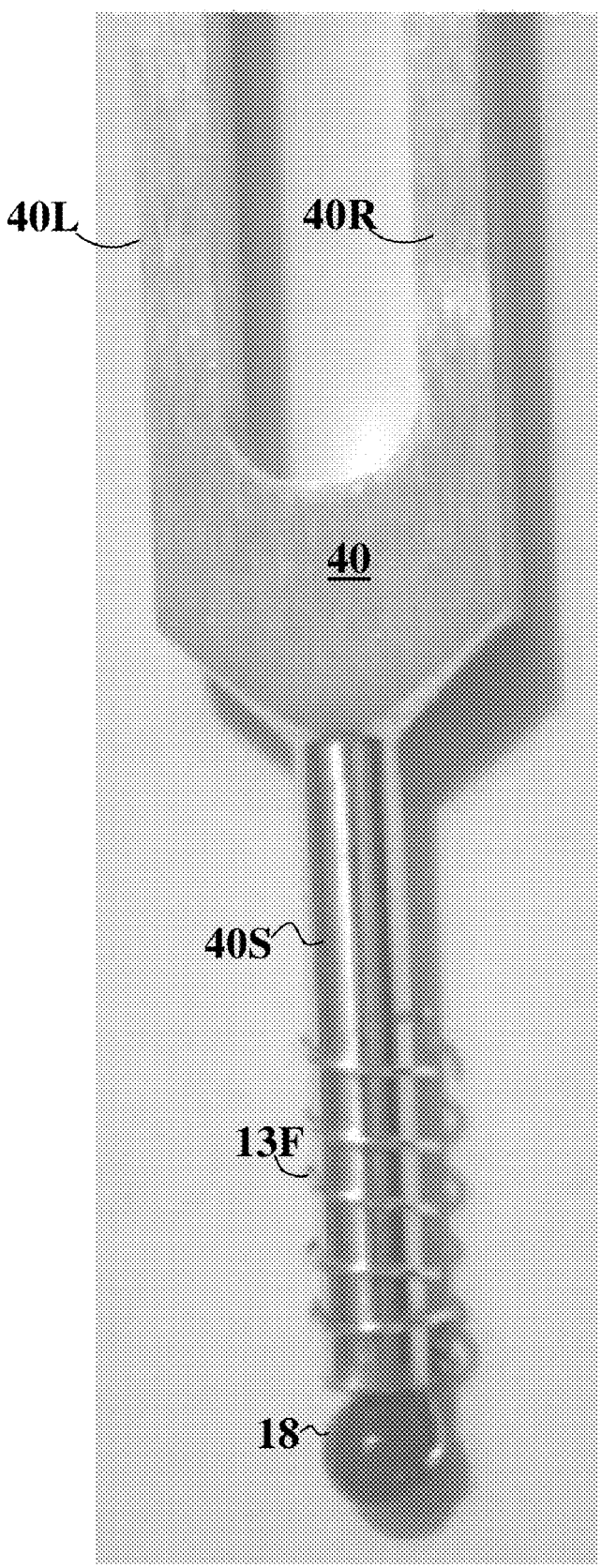
FIG. 11 is a photograph showing that the shaft of the tuning fork of FIG. 10A has been inserted within the hollow space within the helical or spiral metal coil of the acupressure appliance of FIG. 10B so that the vibration of the tuning fork is transmitted into the gem of FIG. 10A.

FIG. 11 is a photograph showing that the shaft 40S of the tuning fork 40 of FIG. 10A has been inserted within the hollow space within the helical or spiral coil 13F of the acupressure appliance of FIG. 10B. The lower end of the shaft 40S is in mechanical contact with the gem 18 of FIG. 10B. Accordingly, vibration of the tuning fork 40 is transmitted into the gem 18.

Figure 12:
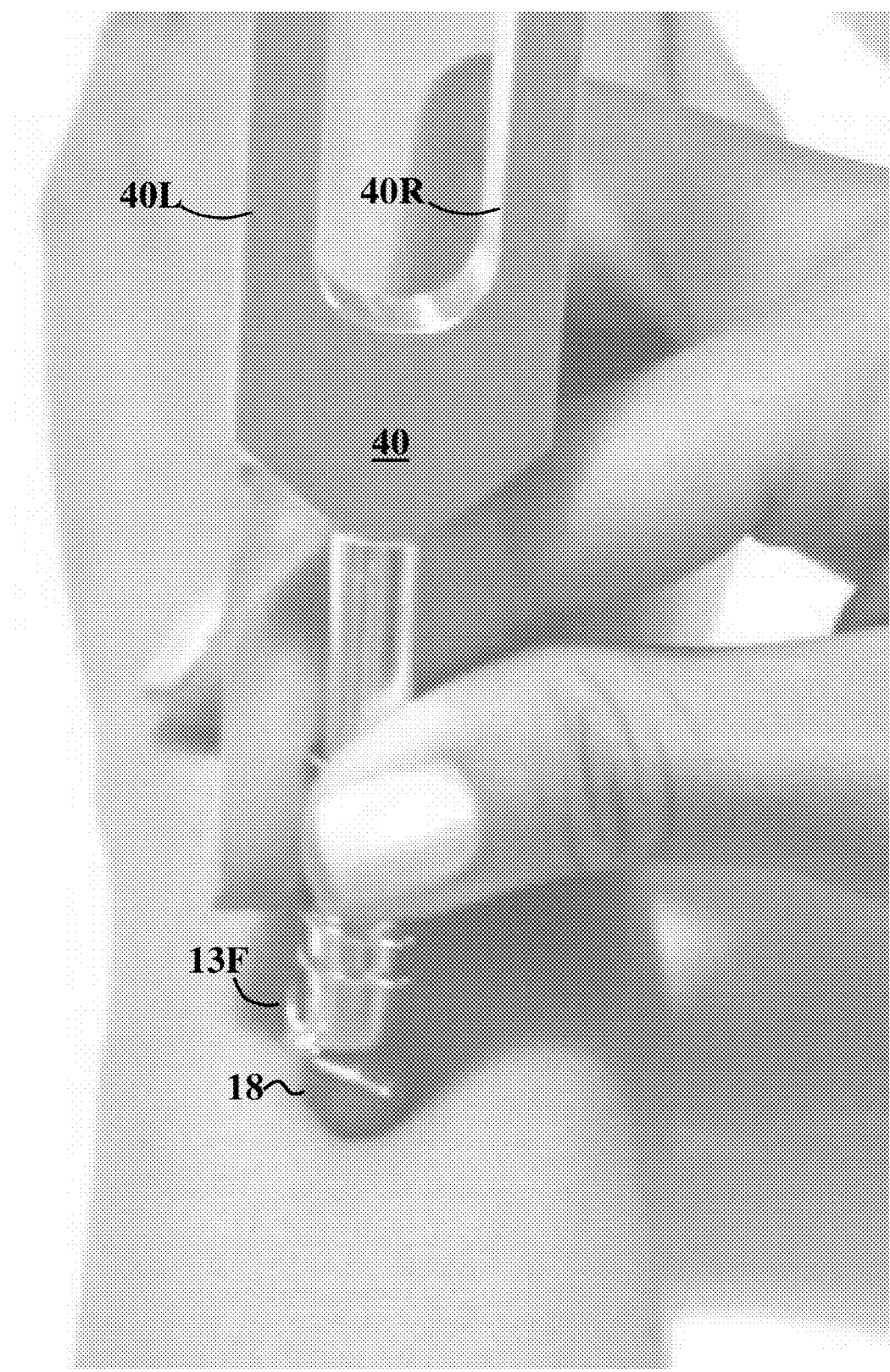
FIG. 12 is a photograph showing the gem of FIGS. 10B and 11 in contact with the lower end of the shaft of the tuning fork and at the same time in contact with an acupoint on the surface of the arm of a patient.

FIG. 12 is a photograph showing the gem 18 of FIGS. 10B and 11 in contact with the lower end of the shaft 40S of the tuning fork 40, and at the same time in contact with an acupoint on the surface of the arm of a patient. The shaft 40S of the tuning fork 40 is being grasped by the thumb and forefinger of the person performing an acupressure treatment on an acupoint on the arm of the patient. It has been discovered that the application of the vibration transmitted from the tuning fork by the interconnection provided by the helical or spiral coil 13F to the gem 18 has greatly enhanced the therapeutic benefit of acupressure.

While this invention has been described in terms of the above specific embodiment(s), those skilled in the art will recognize that the invention can be practiced with modifications within the spirit and scope of the appended claims, i.e. that changes can be made in form and detail, without departing from the spirit and scope of the invention. Accordingly all such changes come within the purview of the present invention and the invention encompasses the subject matter of the claims which follow.

Having thus described the invention, what is claimed as new and desirable to be secured by Letters Patent is as follows:

1. A method of acutreatment comprising:
providing a first element selected from the group consisting of gems and crystals, with said first element being bonded to a mechanical coupling device;
a second element selected from the group consisting of an acupuncture device and a vibratory device;
temporarily joining said mechanical coupling device to said second element thereby forming an acutreatment device; and
then applying said acutreatment device to an acupoint on a patient.

2. The method of claim 1 wherein:
said second element is an acupuncture device; and
said first element is an element selected from the group consisting of gems and crystals.

3. The method of claim 2 wherein said mechanical coupling device is selected from the group consisting of:
i) a helical or spiral, metal wire bonded to said first element;
ii) a metallic cylinder or cone connected to said first element;
iii) a metallic clamp connected to said first element; and
iv) a slidable and/or readily releasable connection to said first element.

4. The method of claim 1 wherein:
said second element is an acupuncture device;
said first element is an element selected from the group consisting of gems and crystals; and
said mechanical coupling device comprises a metal structure bonded to said first element.

5. The method of claim 4 wherein said mechanical coupling device is selected from the group consisting of:
i) a helical or spiral, metal wire bonded to said first element;
ii) a metallic cylinder or cone connected to said first element;
iii) a metallic clamp connected to said first element; and
iv) a slidable and/or readily releasable connection to said first element.

6. The method of claim 1 wherein:
said second element is an acupuncture device;
said first element is an element selected from the group consisting of gems and crystals; and
said mechanical coupling device comprises a helical or spiral, metal wire bonded to said first element.

7. The method of claim 1 wherein:
said second element is an acupressure element selected from the group consisting of gems and crystals; and
said mechanical coupling device comprises a metal structure bonded to said second element.

8. The method of claim 1 wherein said mechanical coupling device comprises a helical or spiral metal wire connected to said first element.

9. The method of claim 1 wherein:
said second element is an acupuncture device,
said first element is an element selected from the group consisting of gems and crystals, and
said mechanical coupling device comprises a metallic cylinder or cone connected to said first element.

10. The method of claim 1 wherein:
said second element is an acupuncture device;
said first element is an element selected from the group consisting of gems and crystals, and said mechanical coupling device comprises a metallic clamp connected to said first element.

11. The method of claim 1 wherein the second element comprises a tuning fork.

12. A method of acutreatment comprising:
providing a first element selected from the group consisting of gems and crystals bonded to a mechanical coupling device;
temporarily joining said mechanical coupling device to a second element selected from the group consisting of an acupuncture needle and a vibratory device; and
then applying said acutreatment device to an acupoint on a patient.

13. The method of claim 12 wherein said second element comprises an acupuncture device.

14. The method of claim 13 wherein the second element comprises a tuning fork.

15. The method of claim 12 wherein:
said second element comprises an acupuncture device; and
said mechanical coupling device comprises a metal structure bonded to said first element.

16. The method of claim 12 wherein:
said second element comprises an acupuncture device; and
said mechanical coupling device comprises a helical or spiral, metal wire bonded to said first element.

17. The method of claim 12 wherein:
said first element comprises is an acupressure element consisting of a gem or a crystal; and
said mechanical coupling device comprises is a metal structure temporarily joined to said second element which comprises a vibratory element.

18. The method of claim 17 wherein the second element comprises a tuning fork.

19. The method of claim 12 wherein the second element comprises a tuning fork.

20. A method of acupuncture treatment comprising:
providing a mechanical coupling device bonded at one end thereof to a first element selected from the group consisting of gems and crystals;
providing an acupuncture needle having a sharp end and a distal end;
providing a temporary assembly of said mechanical coupling device to said distal end of said acupuncture needle; and
then employing said temporary assembly of said first element bonded to said mechanical coupling device and said acupuncture needle in combination to provide an acupuncture treatment.

21. The method of claim 20 wherein said mechanical coupling device comprises a helical or spiral, metal wire bonded to said first element.

* * * * *